United States Patent
Yardibi et al.

(10) Patent No.: US 11,903,774 B2
(45) Date of Patent: Feb. 20, 2024

(54) METHODS AND DEVICES FOR INTERLEAVED SURGICAL IMAGING

(71) Applicant: Cilag GmbH International, Zug (CH)

(72) Inventors: Tarik Yardibi, Wayland, MA (US);
Emir Osmanagic, Raynham, MA (US);
Patrick J. Treado, Pittsburgh, PA (US);
Rick Beideman, Pittsburgh, PA (US);
Matthew P. Nelson, Harrison City, PA (US); Preston Manwaring, Farmington, UT (US)

(73) Assignee: Cilag GmbH International, Zug (CH)

( * ) Notice: Subject to any disclaimer, the term of this patent is extended or adjusted under 35 U.S.C. 154(b) by 135 days.

(21) Appl. No.: 17/464,829

(22) Filed: Sep. 2, 2021

(65) Prior Publication Data
US 2023/0064586 A1    Mar. 2, 2023

(51) Int. Cl.
*A61B 90/00*    (2016.01)
*G06T 11/00*   (2006.01)
*H04N 5/272*   (2006.01)
*A61B 34/30*    (2016.01)
(Continued)

(52) U.S. Cl.
CPC .......... *A61B 90/37* (2016.02); *A61B 90/361* (2016.02); *G06T 11/00* (2013.01); *H04N 5/272* (2013.01); *A61B 1/0005* (2013.01); *A61B 1/3132* (2013.01); *A61B 34/30* (2016.02);
(Continued)

(58) Field of Classification Search
None
See application file for complete search history.

(56) References Cited

U.S. PATENT DOCUMENTS

2007/0276256 A1* 11/2007 Iddan ................ A61B 5/0091
600/473
2009/0005683 A1*  1/2009 Hashimoto .......... G01S 7/5202
600/458
(Continued)

FOREIGN PATENT DOCUMENTS

CN       105982645 B     7/2019

OTHER PUBLICATIONS

International Search Report and Written Opinion received for PCT Application No. PCT/IB2022/058097, dated Nov. 18, 2022, 15 Pages.

*Primary Examiner* — David H Chu
(74) *Attorney, Agent, or Firm* — Mintz Levin Cohn Ferris Glovsky and Popeo, P.C.

(57) ABSTRACT

Systems and methods for receiving data characterizing a plurality of images of a surgical region that includes a first target tissue. The plurality of images include a plurality images associated with visible light images, a plurality of images associated with a first wavelength and a plurality of images associated with the second wavelength that is different from the first wavelength. The method also includes generating a first scene by at least overlaying a first set of images of the plurality of images. The first set of images are temporally contiguous and include a first image associated with the first wavelength, a second image associated with visible light, and a third image associated with the second wavelength. The image further includes generating a second scene by at least overlaying a second set of images of the plurality of images. The second set of images are temporally contiguous.

28 Claims, 5 Drawing Sheets

(51) Int. Cl.
  *A61B 1/00* (2006.01)
  *A61B 1/313* (2006.01)
(52) U.S. Cl.
  CPC ... *A61B 2090/364* (2016.02); *A61B 2090/373* (2016.02); *G06T 2210/41* (2013.01)

(56) References Cited

U.S. PATENT DOCUMENTS

| | | | |
|---|---|---|---|
| 2012/0065518 A1* | 3/2012 | Mangoubi | G06T 7/13 |
| | | | 382/128 |
| 2015/0087955 A1* | 3/2015 | Emelianov | A61B 5/015 |
| | | | 600/407 |
| 2016/0138975 A1 | 5/2016 | Ando et al. | |
| 2018/0368656 A1* | 12/2018 | Austin | A61B 1/0005 |
| 2019/0008387 A1* | 1/2019 | Godavarty | A61B 5/7435 |
| 2020/0309599 A1* | 10/2020 | Aiso | G01J 3/26 |
| 2020/0397259 A1 | 12/2020 | Talbert et al. | |
| 2021/0137375 A1 | 5/2021 | Wisotzky et al. | |

\* cited by examiner

METHODS AND DEVICES FOR INTERLEAVED SURGICAL IMAGING

FIELD

The present disclosure relates generally to interleaved imaging for tissue visualization during surgery.

BACKGROUND

Surgical systems often incorporate an imaging system, which can allow the clinician(s) to view the surgical site and/or one or more portions thereof on one or more displays such as a monitor. The display(s) can be local and/or remote to a surgical theater. An imaging system can include a scope with a camera or sensor that views the surgical site and transmits the view to a display that is viewable by a clinician. Scopes include, but are not limited to, laparoscopes, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes.

For example, certain concealed structures, physical contours, and/or dimensions of structures within a surgical field may be unrecognizable intraoperatively by certain imaging systems. Additionally, certain imaging systems may be incapable of communicating and/or conveying certain information regarding the concealed structures to clinician(s) intraoperatively.

Accordingly, there remains a need for improved imaging techniques for tissue visualization during surgery.

SUMMARY

Various aspects of the disclosed subject matter may provide one or more of the following capabilities.

In an aspect, a method, comprising receiving data characterizing a plurality of images of a surgical region that includes a first target tissue. The plurality of images include a plurality images associated with visible light images, a plurality of images associated with a first wavelength and a plurality of images associated with the second wavelength that is different from the first wavelength. The method also includes generating a first scene by at least overlaying a first set of images of the plurality of images. The first set of images are temporally contiguous and include a first image associated with the first wavelength, a second image associated with visible light, and a third image associated with the second wavelength. The image further includes generating a second scene by at least overlaying a second set of images of the plurality of images. The second set of images are temporally contiguous, and include at least one image from the first set of images. The method also includes displaying the first scene and the second scene, wherein the first and the second scenes are displayed temporally contiguously.

One or more of the following features can be included in any feasible combination.

In some implementations, the at least one image from the first set of images that is included in the second set of images is the third image. In some implementations, generating the first scene includes generating a first tissue image of the first target tissue based on the first image and the third image and overlaying the first tissue image on the second image associated with visible light. In some implementations, the first scene includes a first graphical object superimposed on or adjacent to the first tissue image in the first scene, the first graphical object configured to identify the first tissue image in the first scene. In some implementations, the second set of images includes the third image, a fourth image associated with visible light and a fifth image associated with the first wavelength.

In some implementations, generating the second scene includes generating a second tissue image of the first target tissue based on the third image and the fifth image; overlaying the second tissue image on the fourth image associated with visible light; and updating a location of the first graphical object to superimpose on or adjacent to the second tissue image of the first target tissue in the second scene. The updated first graphical object configured to identify the first target tissue in the second scene. In some implementations, the first, the second and the third images in the first set of images are captured temporally contiguously. The third, the fourth and the fifth images in the second set of images are captured temporally contiguously.

In some implementations, the plurality of visible images are captured at between about 30 frames per second and about 60 frames per second. In some implementations, the plurality of images are captured by a sensor at 60 frames per second and the plurality of visible light images are captured by the sensor at 30 frames per second, and the plurality of images associated with the first and the second wavelength are captured at 30 frames per second. In some implementations, the plurality of images are captured by a sensor at 120 frames per second and the plurality of visible light images are captured by the sensor at 30 frames per second, and the plurality of images associated with the first and the second wavelength captured at 90 frames per second.

In some implementations, the plurality of images comprise a plurality of images associated with a third wavelength that is different from the first wavelength and the second wavelength. The first set of images further include a sixth image associated with the third wavelength, and the at least one image from the first set of images that is included in the second set of images includes the sixth image.

In some implementations, generating the first scene includes generating a first tissue image of the first target tissue based on the first image and the third image, and generating a second tissue image of a second target tissue based on the third image and the sixth image. The surgical region includes the second target tissue. Generating the first scene also includes overlaying the first tissue image and the second tissue image on at least an image associated with visible light temporally contiguous with the third image and/or the sixth image.

In some implementations, generating the second scene includes generating a third tissue image of the first target tissue based on the fifth image and a seventh image associated with the second wavelength. The second set of images includes the seventh image. Generating the second scene also includes generating a fourth tissue image of the second target tissue based on the sixth image and the seventh image and overlaying the third tissue image and the fourth tissue image on at least an image associated with visible light temporally contiguous with the fifth image and/or the seventh image. In some implementations, the plurality of visible images are captured at between about 30 frames per second and about 60 frames per second. In some implementations, the plurality of images are captured by a sensor at 60 frames per second and the plurality of visible light images are captured by the sensor at 30 frames per second, and the plurality of images associated with the first, the second and the third wavelength captured at 30 frames per second.

In some implementations, the plurality of images are captured by a sensor at 120 frames per second and the plurality of visible light images are captured by the sensor at 30 frames per second, and the plurality of images associated with the first and the second wavelength captured at 90 frames per second. In some implementations, the second scene includes a first graphical object superimposed on or adjacent to the third tissue image of the first target tissue in the second scene. The second scene includes a second graphical object superimposed on or adjacent to the fourth tissue image of the second target tissue. In some implementations, the method further includes displaying the first scene and the second scene. The first tissue image and the second image are simultaneously displayed in the first scene.

In some implementations, the at least one image from the first set of images that is included in the second set of images includes the third image and the sixth image. In some implementations, generating the second scene includes generating a sixth tissue image of the first target tissue based on the third image and the fifth image; generating a sixth tissue image of the second target tissue based on the sixth image and the third image; and overlaying the fifth tissue image and the sixth tissue image on at least an image associated with visible light temporally contiguous with the fifth image and/or the sixth image.

In some implementations, the plurality of visible images are captured at between about 30 frames per second and about 60 frames per second. In some implementations, the plurality of images are captured by a sensor at 60 frames per second and the plurality of visible light images are captured by the sensor at 30 frames per second, and the plurality of images associated with the first, the second and the third wavelength are captured at 15 frames per second. In some implementations, the plurality of images are captured by a sensor at 120 frames per second and the plurality of visible light images are captured by the sensor at 30 frames per second, and the plurality of images associated with the first and the second wavelength captured at 90 frames per second. In some implementations, the second scene includes a first graphical object superimposed on or adjacent to the fifth tissue image of the first target tissue in the second scene. The second scene includes a second graphical object superimposed on or adjacent to the sixth tissue image of the second target tissue.

In an aspect, a system includes a single sensor configured to capture a plurality of images of a surgical region comprising a first target tissue. The plurality of images include a plurality of visible light images, first wavelength images and second wavelength images. The system also includes a processor configured to receive data characterizing the plurality of images of a surgical region comprising the first target tissue, the plurality of images comprising a plurality of visible light images, a plurality of first wavelength images and a plurality of second wavelength images. The processor is also configured to generate a first scene by at least overlaying a first set of images of the plurality of images. The first set of images are temporally contiguous and include a first image associated with a first wavelength, a second image associated with visible light, and a third image associated with a second wavelength. The processor is further configured to generate a second scene by at least overlaying a second set of images of the plurality of images. The second set of images are temporally contiguous and include at least one image from the first set of images. The processor is further configured to provide the first combined image and the second combined image. The first and the second combined image are temporally contiguous.

In some implementations, the sensor is operably associated with a surgical instrument. In some implementations, the surgical instrument includes one of an endoscope, a laparoscope, and a robotic vision system.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. Additionally, although terms such as "first" and "second" are used to describe various aspects of a component, e.g., a first end and a second end, such use is not indicative that one component comes before the other. Use of terms of this nature may be used to distinguish two similar components or features, and often such first and second components can be used interchangeably. Still further, a number of terms may be used throughout the disclosure interchangeably but will be understood by a person skilled in the art.

The present disclosure is directed to a surgical imaging system that leverages illumination of visible-light and multiple electromagnetic radiations on a surgical region to identify one or more tissues therein (e.g., in real-time). For example, a target tissue in the surgical region can be more responsive (e.g., absorb, reflect, etc.) to a set of electromagnetic radiations than visible light. As a result, the target tissue may be detected by the set of electromagnetic radiations which may not have been possible by visible light alone. In some implementations, the surgical imaging system can generate a scene of the surgical region by combining a visible light image (generated from visible light) and a target tissue image (generated from the set of electromagnetic radiations) and present the scene to a user (e.g., a surgeon) in real-time. This can allow the user to identify the target tissue during a procedure (e.g., surgery).

In some implementations, the surgical region can be sequentially illuminated by the visible-light and the set of electromagnetic radiations in a sequence. Images corresponding to the various illuminations in the sequence can be captured by a single image sensor (e.g., an image sensor with high spectral bandwidth). A scene can be generated based on two or more images. In some implementations, two or more images generated by the illumination sequence can be overlaid to generate a scene. For example, images of the surgical region generated by electromagnetic radiations having a first wavelength and a second wavelength (that interact with a given tissue) can be superimposed on a visible light image of the surgical region. The resulting scene represents an image of the surgical region where the given tissue has been identified. The scene can be displayed (e.g., in a graphical user interface [GUI]) and can help a user of the surgical imaging system (e.g., a surgeon) to identify the given tissue (e.g., during surgery). This may not have been possible with the visible light image alone.

In existing systems, it typically requires a significant amount of time to combine multiple images to generate a scene. For example, the surgical region may have to be sequentially illuminated by visible light and multiple electromagnetic radiations, and the corresponding images need to be acquired and superimposed by a processor. This can result in considerable delay in displaying consecutive scenes which can impact the viewing experience of the user. For example, during a surgery, the real-time display of the surgical region may not appear to be seamless (e.g., when the frame per second (fps) of visible light images is less than 24-30 FPS). Furthermore, if there are more than one tissues to be identified in the surgical region, multiple electromagnetic radiations may be needed (e.g., more than two wavelengths) that can further slow the illumination, image acquisition and scene generation of the surgical region, and can result in greater delay between consecutive scene generation.

In some implementation of the system disclosed herein, such delay can be reduced by using one or more image from one scene in the generation of another scene (e.g., in consecutive scenes). This can result in a seamless viewing of the surgical region. Furthermore, images associated with various wavelengths and visible light are captured by a single image sensor coupled to a surgical instrument. This obviates the need to include multiple image sensors to capture images associated with the different wavelengths, something that might not even be possible without making the surgical instrument unwieldy and impractical.

Figure 1:
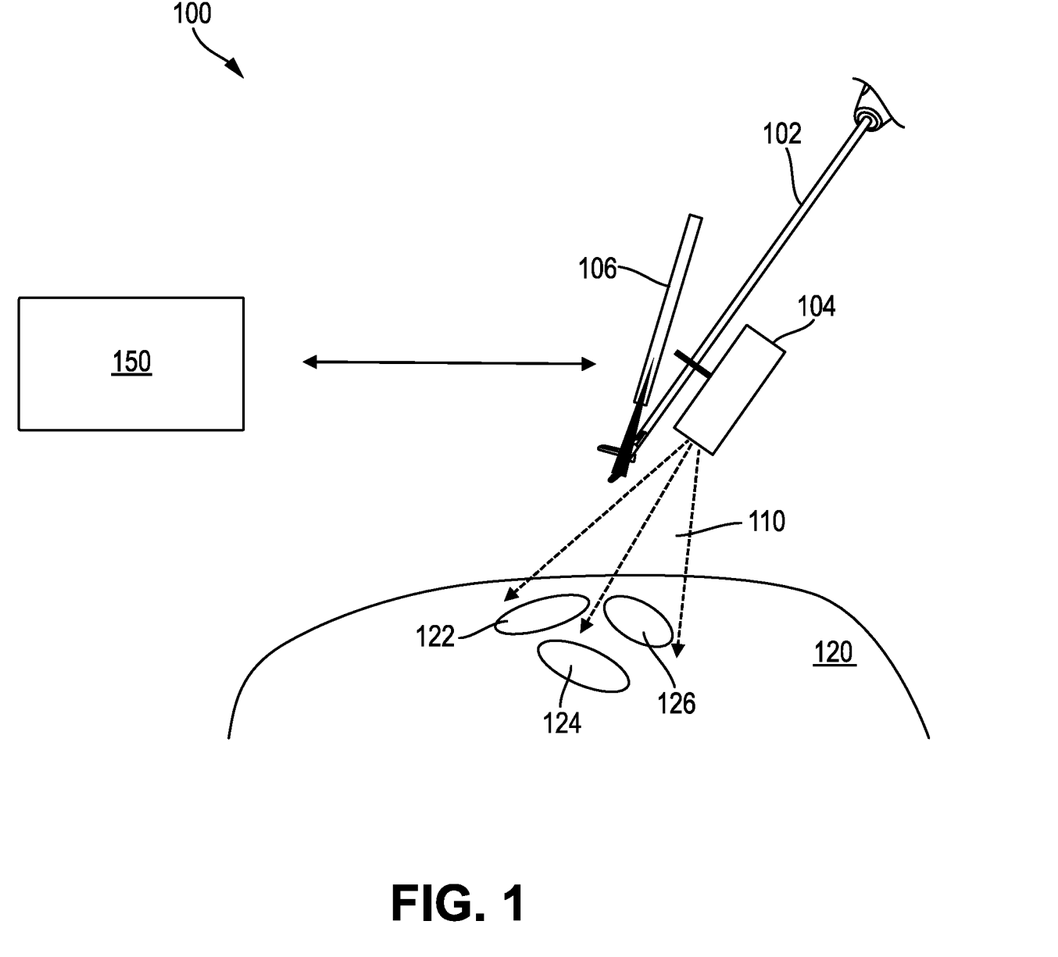
FIG. 1 illustrates an exemplary surgical imaging system configured to perform multi-wavelength imaging of a surgical region during a surgical procedure, according to at least one aspect of the present disclosure.

FIG. 1 illustrates an exemplary surgical imaging system 100 configured to perform multi-wavelength imaging of a surgical region 120 during a surgical procedure. The surgical imaging system 100 can include a surgical instrument 102, a source 104 and an image sensor 106. In some implementations, the source 104 and an image sensor 106 can be coupled to the surgical instrument 102 (e.g., an endoscope, a laparoscope, a robotic vision system, etc.). The source 104 can include multiple radiation sources associated with electromagnetic radiation of multiple wavelengths and visible light. The surgical imaging system can further include a control system 150 that can be operationally coupled to the source 104 and the image sensor 106. The control system 150 can control the operation of the image sensor 106 and source 104, and process the images acquired by the sensor 106.

The surgical region 120 can include multiple target tissues that can be imaged by radiation 110 generated by the source 104 that can include multiple wavelengths. For example a first target tissue 122 can be imaged by a first wavelength and a second wavelength, a second target tissue 124 can be imaged by the second wavelength and a third wavelength, and a third target tissue 126 can be imaged by the third wavelength and a fourth wavelength. Additionally, visible light image of the surgical region 120 can be acquired by visible light generated by the source 104. The surgical imaging system 100 and the surgical region 120 are exemplary. In some implementations, the surgical region 120 can have fewer than three target tissues (e.g., one target tissue, two target tissues) or more than three target tissues (e.g., four target tissues, five target tissues, etc.). In some implementations, the surgical system 100 can include multiple sources (for generating radiation of different wavelengths) that are coupled to the surgical instrument 102 at different locations.

Figure 2:
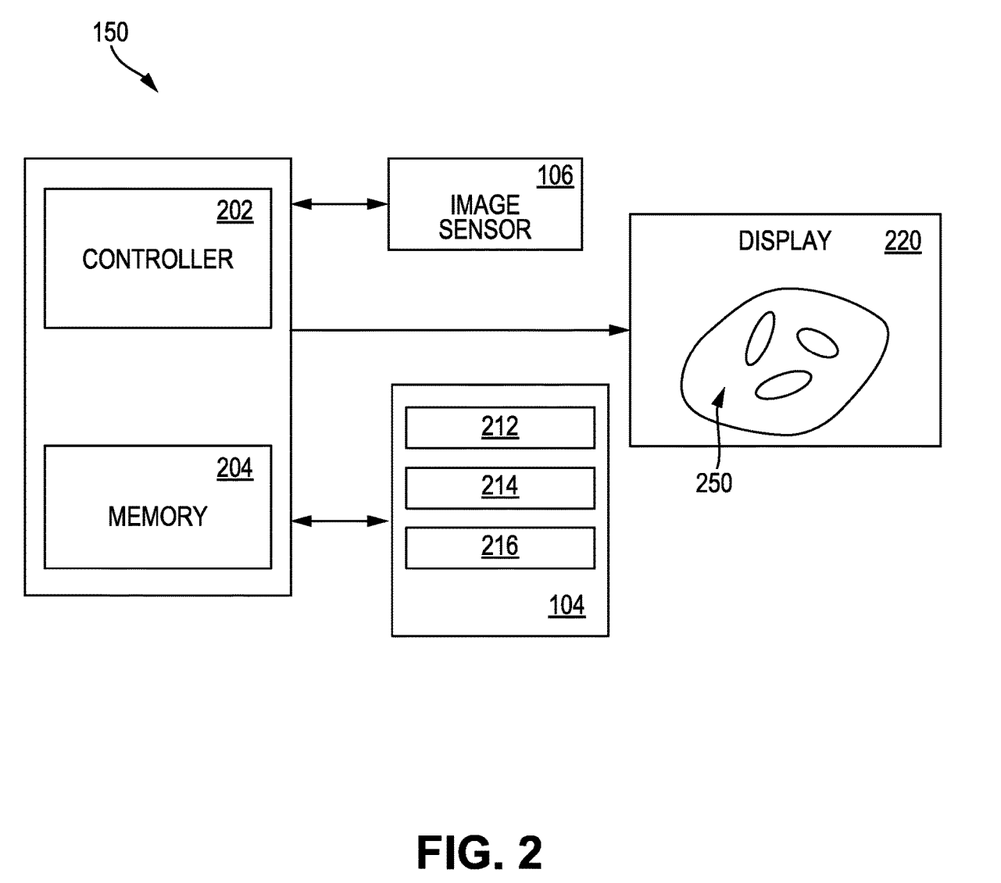
FIG. 2 is a schematic illustration of the exemplary control system of the surgical visualization system in FIG. 1.

FIG. 2 is a schematic illustration of the exemplary control system 150 of the surgical visualization system 100. As shown, the control system 200 includes a controller 202 having at least one processor that is in operable communication with, among other components, a memory 204, various radiation sources 212-216 (e.g., included in the source 104), the image sensor 106, and the display 220. The memory 204 is configured to store instructions executable by the processor of the controller 204 to overlay images associated with various wavelengths to generate one or more scenes, identify target tissues (e.g., target tissues 122-126) in the surgical region in the scene, provide the scenes to the display 220 to be displayed (e.g., in a graphical user interface (GUI) on the display 220).

The controller 202 can instruct the radiation sources 212-216 (e.g., visible light source 212, first wavelength source 214, second wavelength source 216, etc.) to sequentially generate and direct radiation at the surgical region 120 and can instruct the image sensor 106 to acquire the corresponding image. For example, in order to capture a visible light image, the visible light source 212 and image sensor 106 are activated during a first time period. Similarly, a first wavelength image (or a second wavelength image) can be acquired by activating the image sensor 106 and first wavelength source 214 (or the second wavelength source 216) during a second time period (or a third time period). In some implementations, every alternate image that is captured by the image sensor can be a visible light image. For example, for five temporally consecutive time periods, a visible light image is captured during the first, third and fifth time periods, the first wavelength image is captured during the second time period and the second wavelength image is captured during the fourth time period.

The controller 202 can determine the order in which various wavelengths/visible light is illuminated on the surgical region. For example, as discussed above, visible light can be illuminated on the surgical region 120 during alternate time periods. The various ordering of illumination of surgical region by electromagnetic radiation of different wavelengths is described below. The controller 202 can determine the duration of the various time periods associated with the exposure of the surgical region 120 to the visible light/various wavelengths. The duration of the various time periods can be related to the rate at which the image sensor 106 captures the various images (also referred to as frames per second (fps)). For example, the image sensor 106 can be configured to capture images at 60 fps, 90 fps, 120 fps, etc. In some implementations, the image capture rate can be set such that the fps associated with visible light image is at least 30 fps. For example, for a 60 fps image sensor, every second image (or frame) is a visible light image. Alternately, for a 120 fps image sensor every fourth image (or frame) is a visible light image.

Figure 3:
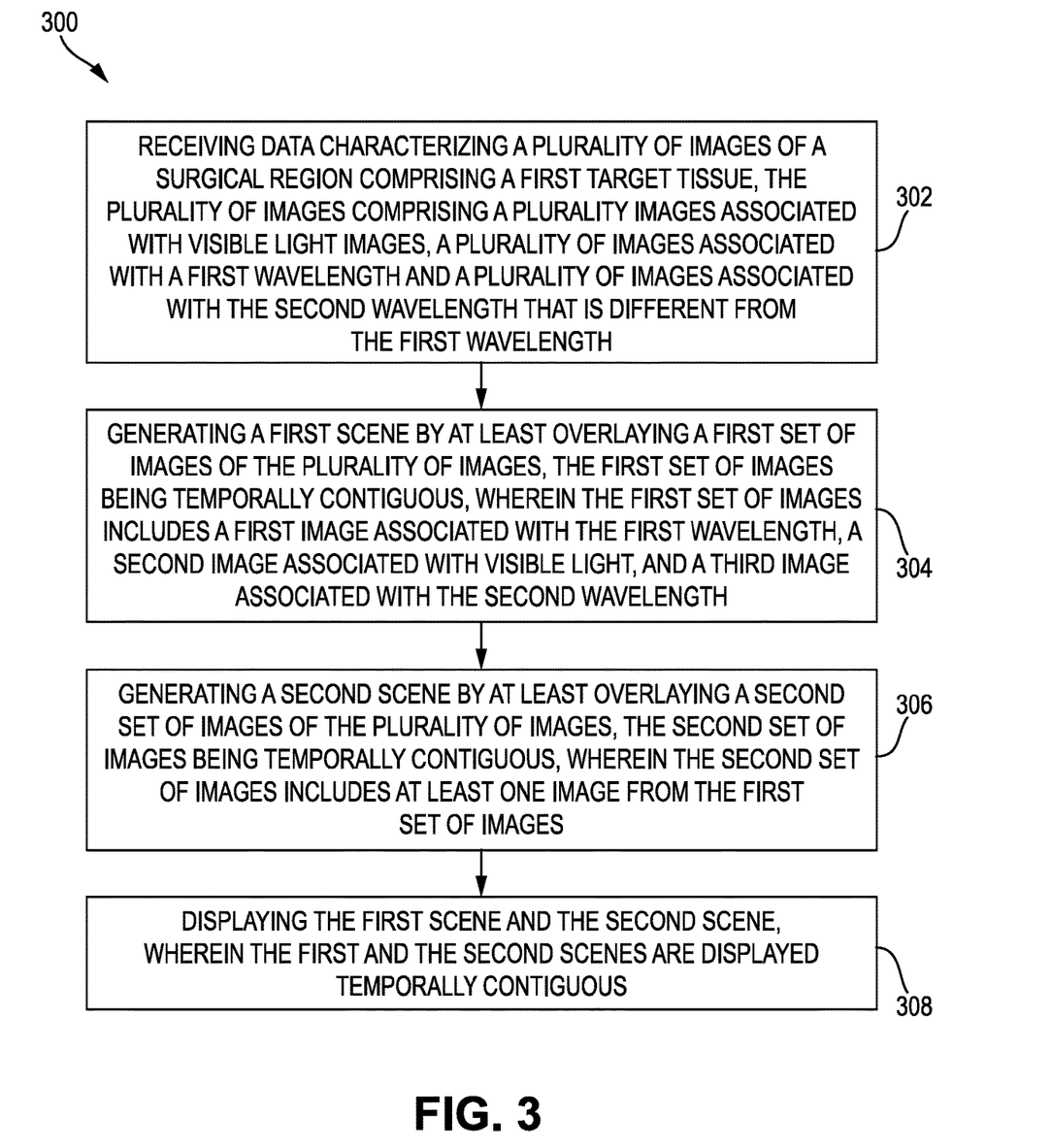
FIG. 3 is a flowchart illustrating an exemplary method of generating temporally consecutive scenes.

FIG. 3 is a flowchart illustrating an exemplary method of generating temporally consecutive scenes. At step 302 data characterizing a plurality of images of a surgical region (e.g., surgical region 120) that includes one or more target tissues (e.g., a target tissues 122-126) can be received (e.g., by the controller 202). The plurality of images can include a plurality images associated with visible light images, a plurality of images associated with a first wavelength and a plurality of images associated with the second wavelength that is different from the first wavelength.

Figure 4:
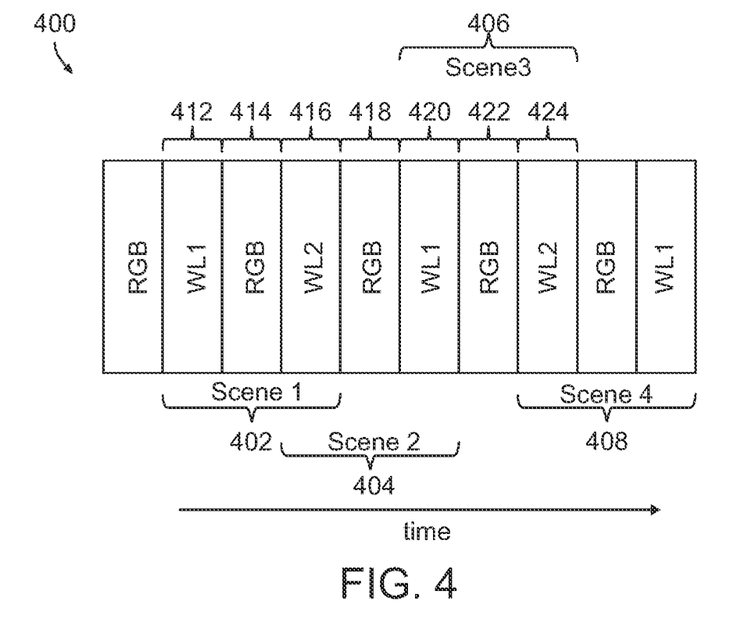
FIG. 4 illustrates an exemplary illumination sequence of visible light, a first wavelength radiation and a second wavelength radiation that are sequentially illuminated at the surgical region.

FIG. 4 illustrates an exemplary illumination sequence 400 of visible light (or RGB), a first wavelength radiation (or first wavelength WL1) and a second wavelength radiation (or second wavelength WL2) that are sequentially illuminated at the surgical region. For example, the first target tissue 122 in the surgical region 120 can interact with WL1 and WL2 (or a portion thereof). In some implementations, the first target tissue 122 can reflect WL1 and WL2 (or a portion thereof) and the reflected portion can be captured by the image sensor 106. In some implementations, the target tissue 122 can generate a new wavelength radiation based on the interaction with WL1 and WL2 (e.g., a fluorophore in the target tissue 122 can generate fluorescence radiation based on the interaction with WL1 and WL2). The new wavelength radiation can be detected by the image sensor 106.

As illustrated in FIG. 4, the total illumination time can include multiple sub-periods 412-422. During each of these time periods, one of the visible light, WL1 and WL2 is illuminated on the surgical region. As illustrated in FIG. 4, visible light is illuminated in alternate sub-periods 414, 418 and 422. WL1 and WL2 are illuminated between two sub-periods of visible light illumination. For example, WL1 is illuminated in sub-periods 412 and 420; and WL2 is illuminated in sub-periods 416 and 424.

Returning back to FIG. 3, at step 304, a first scene 402 can be generated by at least overlaying a first set of images of the plurality of images acquired by the image sensor (e.g., image sensor 106) based on the illumination of the surgical region by a portion of the illumination sequence 400 (e.g., illumination during sub-periods 412, 414 and 416). For example, the first set of images can include a first image associated with WL1 illuminated during sub-period 412, a second image associated with visible light illuminated during sub-period 414, and a third image associated with WL2 illuminated during sub-period 416. As illustrated in FIG. 4, the sub-periods 412, 414 and 416 are temporally contiguous.

In some implementations, generating the first scene 402 can include generating a first tissue image of the first target tissue 122 based on the first image associated with WL1 and the third image associated with WL2. As discussed above, the first target tissue 122 can interact with WL1 during the sub-period 412 and reflect a portion thereof and/or generate a new radiation with a different wavelength. This reflected/generated radiation can be captured by the image sensor 106 (during the sub-period 412) resulting in the generation of the first image. Data associated with the first image can be received by the controller 202 (e.g., as described in step 302). Additionally, the first target tissue 122 can interact with WL2 during the sub-period 416 and reflect a portion thereof and/or generate a new radiation with a different wavelength. This reflected/generated radiation can be captured by the image sensor 106 (during the sub-period 416) resulting in the generation of the third image. Data associated with the first image can be received by the controller 202 (e.g., as described in step 302). The controller 202 can generate the first tissue image from the first image and the third image (e.g., by superposing the first image and the third image).

The surgical region 120 can interact with visible light during the sub-period 414 and reflect a portion thereof. This reflected portion of the visible light can be captured by the image sensor 106 (during the sub-period 414) resulting in the generation of the second image. Data associated with the second image can be received by the controller 202 (e.g., as described in step 302). The first tissue image generated from the first image and the third image can be overlaid on the second image associated with visible light to generate the first scene 402. The first scene 402 can be a visible light image of the surgical region 120 that illustrate the first target tissue (e.g., via the first target tissue image in the first scene 402) which may not have been visible from the visible light image of the surgical region alone. In some implementations, the first scene 402 can include a graphical object superimposed on or adjacent to the first tissue image in the first scene 402. For example, the graphical object can be an indicator (e.g., an arrow) that can point at the first tissue image, an outline that can surround the first tissue image, etc.

Returning back to FIG. 3, at step 306, a second scene 404 can be generated by at least overlaying a second set of images of the plurality of images acquired by the image sensor (e.g., image sensor 106) based on the illumination of the surgical region by a portion of the illumination sequence 400 (e.g., illumination during sub-periods 416, 418 and 420). For example, the second set of images can include the third image associated with WL2 illuminated during sub-period 416, a fourth image associated with visible light illuminated during sub-period 418, and a fifth image associated with WL1 illuminated during sub-period 420. As illustrated in FIG. 4, the sub-periods 416, 418 and 420 are temporally contiguous. Generation of the second scene 404 is based on the third image associated with WL2 that is also used in the generation of the first scene 402. As a result, a new image associated with WL2 that would involve illuminating the surgical region 120 again (e.g., during an additional sub-period) is not needed. This can reduce the delay between the generation of the first scene 402 and the second scene 404.

In some implementations, generating the second scene 404 can include generating a second tissue image of the first target tissue 122 based on the third image associated with WL2 and the fifth image associated with WL1. The first target tissue 122 can interact with WL1 and the image sensor 106 can capture the corresponding fifth image (e.g., during the sub-period 420). Data associated with the fifth image can be received by the controller 202 (e.g., as described in step 302). Data associated with the fifth image can be received by the controller 202 (e.g., as described in step 302). The controller 202 can generate the second tissue image from the fifth image and the third image (e.g., by superposing the fifth image and the third image). The fourth image can be acquired based on illumination of the surgical region 120 with visible light during the sub-period 418. Data associated with the fourth image can be received by the controller 202 (e.g., as described in step 302). The second tissue image of the first target tissue can be generated from the fifth image and the third image, and can be overlaid on the fourth image associated with visible light to generate the second scene 404. In some implementations, the first graphical object of the first scene 402 can be updated to superimpose on or adjacent to the second tissue image. For example, the location of the first graphical object can be updated as the location of the image of the first target tissue moves from the first scene 402 to the second scene 404. The graphical object can be an indicator (e.g., an arrow) that can point at the second tissue image, an outline that can surround the second tissue image, etc.

In some implementations, multiple scenes of the surgical region 120 can be generated based on the illumination sequence. Temporally consecutive scenes can share at least one image associated with WL1 or WL2. For example, a third scene 406 can be generated that can be based on the fifth image (generated from WL1 illumination during the sub-period 420) and visible light image and image associated with WL2 in sub-periods 422 and 424, respectively. In some implementations, every second image is a visible light image and every fourth image is a WL1 image or a WL2 image. In other words, visible light can be illuminated on the surgical region 120 during alternate time periods, and WL1/WL2 are illuminated on the surgical region during every fourth time period.

Returning back to FIG. 3, at step 308 the first scene and the second scene can be displayed (e.g., on display 220). The first and the second scenes are displayed temporally contiguously. For example, the controller 202 can provide the first scene and the second scene to the display 220. As illustrated in FIG. 2, the display can display a scene 250 associated with the surgical region 120. The scene 250 can include an image with the target tissue 122 in the surgical region. In some implementations, the scene 250 can include multiple target tissue images associated with other target tissues (e.g., target tissues 124, 126, etc.) in the surgical region (e.g., generated by illumination sequence described in FIG. 5 and FIG. 6).

Figure 5:
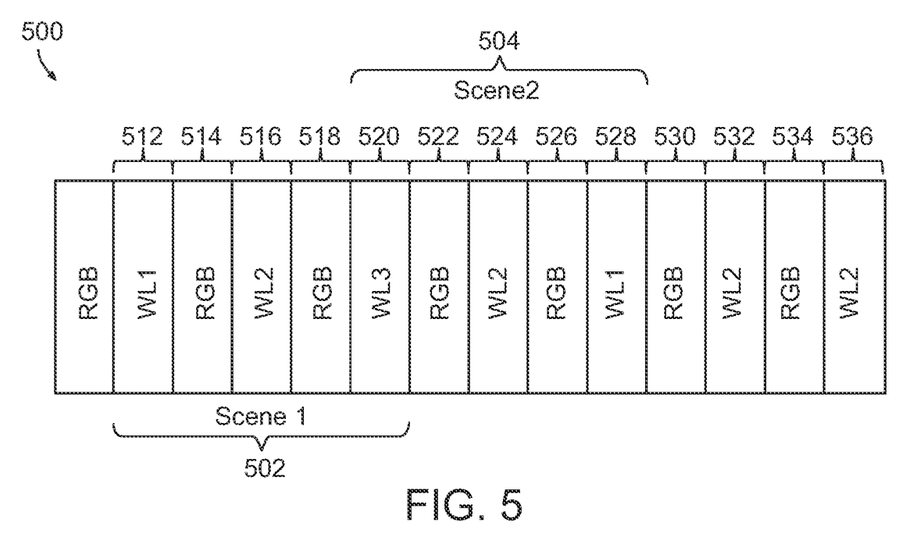
FIG. 5 illustrates an exemplary illumination sequence of visible light, the first wavelength radiation, the second wavelength radiation and a third wavelength radiation that are sequentially illuminated at the surgical region.

In some implementations, the surgical region can include two target tissues. Scenes of the surgical region that includes the two target tissues can be generated by illuminating the surgical region with visible light, and three electromagnetic radiations having three wavelengths (e.g., three distinct wavelength). FIG. 5 illustrates an exemplary illumination sequence 500 of visible light (or RGB), the first wavelength radiation (or first wavelength WL1), the second wavelength radiation (or second wavelength WL2), and a third wavelength radiation (or third wavelength WL3) that are sequentially illuminated at the surgical region (e.g., surgical region 120). For example, the first target tissue 122 in the surgical region 120 can interact with WL1 and WL2 (or a portion thereof) and the second target tissue 124 in the surgical region 120 can interact with WL2 and WL3 (or a portion thereof). As described above, interaction can include reflection of a portion of incident wavelengths (e.g., WL1 and WL2 for first target tissue 122, WL2 and WL3 for second target tissue 124, etc.) or generation of a new wavelength(s) that can be detected by the image sensor 106.

As illustrated in FIG. 5, the total illumination time can include multiple sub-periods 512-536. During each of the sub-periods, one of the visible light, WL1, WL2 or WL3 (which are different from each other) can be illuminated on the surgical region. For example, visible light is illuminated in alternate sub-periods 514, 518, 522, 526 and 530. WL1, WL2 and WL3 are illuminated between two sub-periods of visible light illumination. For example, WL1 is illuminated in sub-periods 512 and 528; WL2 is illuminated in sub-periods 516, 524 and 532; and WL3 is illuminated in sub-periods 520 and 536. A scene of the surgical region, which includes a visible image of the surgical region where the first and second target tissues are identified, can be generated by overlaying images associated with visible light, WL1, WL2 and WL3. For example, the first scene 502 can be generated from a first set of images acquired during the illumination of the surgical region in sub-periods 512-520 which includes visible light images acquired during sub-periods 514 and 518, WL1 image acquired during sub-period 512, WL2 image acquired during sub-period 516, and WL3 image acquired during sub-period 520.

In some implementations, generation of the first scene 502 can include generating a first tissue image of the first target tissue (e.g., first target tissue 122) and a second tissue image of the second target tissue (e.g., second target tissue 122) in the surgical region. For example, the first tissue image of the first target tissue 122 can be generated based on the image associated with WL1 (illuminated during sub-period 512) and the image associated with WL2 (illuminated during sub-period 516). The second tissue image of the second target tissue 124 can be generated based on the image associated with WL2 (illuminated during sub-period 516) and the image associated with WL3 (illuminated during sub-period 520). The first and second tissue images can be generated by the controller 202 based on images acquired by the image sensor 106 (e.g., during sub-periods 512, 516 and 520).

The first tissue image and the second tissue image can be overlaid on the visible light image acquired during time-period temporally contiguous with one or more of the sub-periods 512, 516 and 520 (associated with WL1, WL2 and WL3, respectively). For example, the first and second tissue images can be overlaid on one of the visible light images acquired during the sub-periods 514 and 518. As a result, the first and the second tissue images can be simultaneously displayed in the second scene 504. In some implementations, the first and the second tissue images are overlaid on the visible light image acquired most recently in the first set of images (e.g., visible light image in sub-period 518). In some implementations, the first scene 502 can include a first graphical object superimposed on or adjacent to the first tissue image in the first scene 502 and a second graphical object superimposed on or adjacent to the second tissue image in the first scene 502. For example, the first (or second) graphical object can be an indicator (e.g., an arrow) that can point at the first (or second) tissue image, an outline that can surround the first (or second) tissue image, etc.

The second scene 504 can be generated from a second set of images acquired during the illumination of the surgical region in sub-periods 520-528 which includes visible light images acquired during 522 and 526, WL1 image acquired during 528, WL2 image acquired during 524, and WL3 image acquired during 520. Generation of the second scene 504 is based on the WL3 image acquired during sub-period 520 that is also used in the generation of the first scene 502. As a result, a new image associated with WL3 that would involve illuminating the surgical region 120 again (e.g., during an additional sub-period) is not needed. This can reduce the delay between the generation of the first scene 502 and the second scene 504. As a result, a new image associated with WL3 that would involve illuminating the surgical region again (e.g., during an additional sub-period) is not needed. This can reduce the delay between the generation of the first scene 502 and the second scene 504.

In some implementations, generation of the scene 504 can include generating a third tissue image of the first target tissue (e.g., first target tissue 122) and a fourth tissue image of the second target tissue (e.g., second target tissue 122) in the surgical region. The third tissue image can represent a temporal progression in the visualization of the first target tissue from the first scene 502 (which includes the first tissue image of the first target tissue) to the second scene 504. Similarly, the fourth tissue image can represent a temporal progression in the visualization of the second target tissue from the first scene 502 (which includes the second tissue image of the second target tissue) to the second scene 504. In some implementations, the temporal progression in the visualization of the first (or second) target tissue can result from the relative movement between the first (or second) target tissue and the image sensor (e.g., during surgery as the surgical instrument 102 moved).

The third tissue image of the first target tissue 122 can be generated based on the image associated with WL1 (illuminated during sub-period 528) and the image associated with WL2 (illuminated during sub-period 524). The fourth tissue image of the second target tissue 124 can be generated based on the image associated with WL2 (illuminated during sub-period 524) and the image associated with WL3 (illuminated during sub-period 520). The third and fourth tissue images can be generated by the controller 202 based on images acquired by the image sensor 106 (e.g., during sub-periods 520, 524 and 528).

The third tissue image and the fourth tissue image can be overlaid on the visible light image acquired during time-period temporally contiguous with one or more of the sub-periods 520, 524 and 528 (associated with WL1, WL2 and WL3, respectively). For example, the third and fourth tissue images can be overlaid on one of the visible light images acquired during the sub-periods 522 and 526. In some implementations, the first graphical object in the first scene 502 can be updated to superimpose on or adjacent to the third tissue image in the second scene 504, and the second graphical object in the first scene 502 can be updated to superimpose on or adjacent to the fourth tissue image in the second scene 504. For example, the location of the first (or second) graphical object can be updated as the location of the image of the first (or second) target tissue temporally progresses (e.g., moves) from the first scene 502 to the second scene 504. The first (or second) graphical object can be an indicator (e.g., an arrow) that can point at the third (or fourth) tissue image, an outline that can surround the third (or fourth) tissue image, etc.

Figure 6:
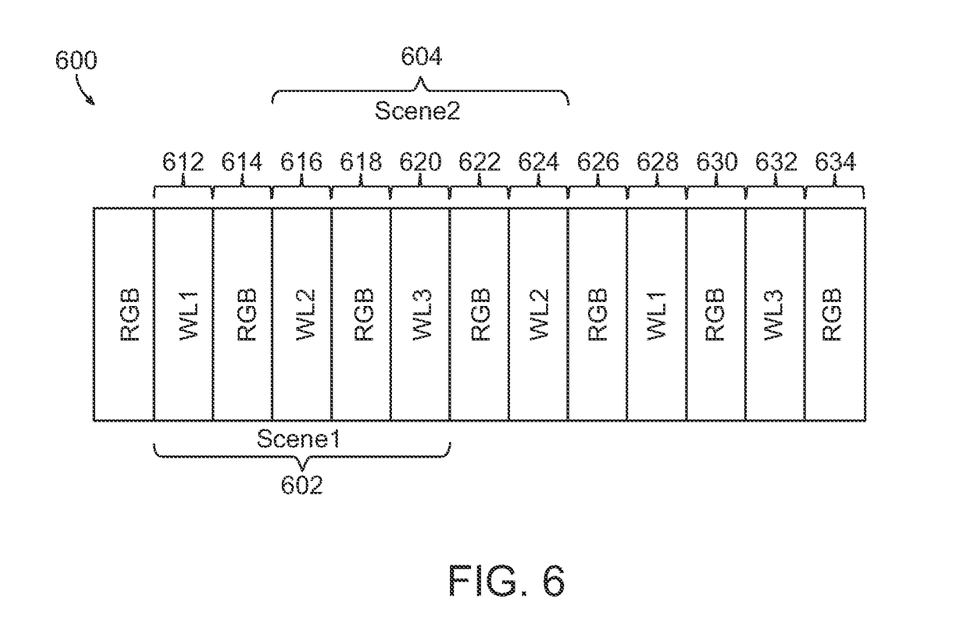
FIG. 6 illustrates another exemplary illumination sequence of visible light, the first wavelength radiation, the second wavelength radiation and a third wavelength radiation that are sequentially illuminated at the surgical region.

FIG. 6 illustrates another exemplary illumination sequence 600 of visible light (or RGB), the first wavelength radiation (or first wavelength WL1), the second wavelength radiation (or second wavelength WL2), and a third wavelength radiation (or third wavelength WL3) that are sequentially illuminated at the surgical region (e.g., surgical region 120). The first target tissue in the surgical region can interact with WL1 and WL3 (or a portion thereof) and the second target tissue in the surgical region can interact with WL2 and WL3 (or a portion thereof).

The temporal arrangement of illumination sub-periods associated with WL1, WL2 and WL3 in illumination sequence 600 is different relative to the illumination sequence 500. For example, visible light is illuminated in alternate sub-periods 614, 618, 622, 626 and 630. WL1, WL2 and WL3 are illuminated between two sub-periods of visible light illumination. For example, WL1 is illuminated in sub-periods 612 and 624; WL2 is illuminated in sub-periods 616 and 628; and WL3 is illuminated in sub-periods 620 and 632. A scene of the surgical region, which includes a visible image of the surgical region where the first and second target tissues are identified, can be generated by overlaying images associated with visible light, WL1, WL2 and WL3. For example, the first scene 602 can be generated from a first set of images acquired during the illumination of the surgical region in sub-periods 612-620 which includes visible light images acquired during sub-periods 614 and 618, WL1 image acquired during sub-period 612, WL2 image acquired during sub-period 616, and WL3 image acquired during sub-period 620.

In some implementations, generation of the first scene 602 can include generating a first tissue image of the first target tissue (e.g., first target tissue 122) and a second tissue image of the second target tissue (e.g., second target tissue 122) in the surgical region. For example, the first tissue image of the first target tissue can be generated based on the image associated with WL1 (illuminated during sub-period 612) and the image associated with WL3 (illuminated during sub-period 620). The second tissue image of the second target tissue can be generated based on the image associated with WL2 (illuminated during sub-period 616) and the image associated with WL3 (illuminated during sub-period 620). The first and second tissue images can be generated by the controller 202 based on images acquired by the image sensor 106 (e.g., during sub-periods 612, 616 and 620).

The first tissue image and the second tissue image can be overlaid on the visible light image acquired during time-period temporally contiguous with one or more of the sub-periods 612, 616 and 620 (associated with WL1, WL2 and WL3, respectively). For example, the first and second tissue images can be overlaid on one of the visible light images acquired during the sub-periods 614 and 618. As a result, the first and the second tissue images can be simultaneously displayed in the second scene 604. In some implementations, the first and the second tissue images are overlaid on the visible light image acquired most recently in the first set of images (e.g., visible light image in sub-period 618). In some implementations, the first scene 602 can include a first graphical object superimposed on or adjacent to the first tissue image in the first scene 602 and a second graphical object superimposed on or adjacent to the second tissue image in the first scene 602. For example, the first (or second) graphical object can be an indicator (e.g., an arrow) that can point at the first (or second) tissue image, an outline that can surround the first (or second) tissue image, etc.

The second scene 604 can be generated from a second set of images acquired during the illumination of the surgical region in sub-periods 616-624 which includes visible light images acquired during sub-periods 618 and 622, WL1 image acquired during sub-period 624, WL2 image acquired during 616, and WL3 image acquired during 620. Generation of the second scene 604 is based on the WL2 image and WL3 image (associated with the second target tissue) acquired during sub-periods 616 and 620, respectively, which are also used in the generation of the first scene 602. This schema can reduce the delay between the generation of the first scene 602 and the second scene 604. The reduction in delay can be achieved, for example, because generation of the scene 604 involves generating a new tissue image (or a third tissue image) of the first target tissue while reusing the second tissue image (of the second target tissue) from the first scene. In other words, while the third tissue image can represent a temporal progression in the visualization of the first target tissue from the first scene 602 (which includes the first tissue image of the first target tissue) to the second scene 604, a temporal progression in the visualization of the second target tissue is not achieved between the first scene 602 and the second scene 604. The third tissue image of the first target tissue can be generated based on the image associated with WL1 (illuminated during sub-period 624) and the image associated with WL3 (illuminated during sub-period 620). The third tissue images can be generated by the controller 202 based on images acquired by the image sensor 106 (e.g., during sub-periods 620 and 624).

The third tissue image can be overlaid on the visible light image acquired during time-period temporally contiguous with one or more of the sub-periods 620, and 624 (associated with WL3 and WL1, respectively). For example, the third tissue images can be overlaid on one of the visible light images acquired during the sub-periods 622 and 626. In some implementations, the first graphical object in the first scene 602 can be updated to superimpose on or adjacent to the third tissue image in the second scene 604. For example, the location of the first graphical object can be updated as the location of the image of the first target tissue temporally progresses (e.g., moves) from the first scene 602 to the second scene 604. The first graphical object can be an indicator (e.g., an arrow) that can point at the third (or fourth) tissue image, an outline that can surround the third (or fourth) tissue image, etc.

The duration of the sub-periods in illumination sequence 400, 500, 600, etc., can be varied. In some implementations, the duration of the sub-periods can be associated with the number of frames per second (fps) that the image sensor acquires. For example, for a 60 fps image sensor, the duration of the sub-period can be about 16.6 millisecond. Alternately, for a 120 fps image sensor, the duration of the sub-period can be about 8.33 milliseconds. In some implementations, seamless viewing of the surgical region can be achieved by setting the visible image frames per second at about 30 fps. In other words, if a 60 fps image sensor is used, every second frame can be associated with acquisition of visible light image. The remaining frames (e.g., 30 fps) can be associated with the acquisition of images associated with WL1, WL2, WL3, etc. Alternately, if a 90 fps image sensor is used, every third frame can be associated with acquisition of visible light image. The remaining frames (e.g., 60 fps) can be associated with the acquisition of images associated with WL1, WL2, WL3, etc. Alternately, if a 120 fps image sensor is used, every fourth frame can be associated with acquisition of visible light image. The remaining frames (e.g., 90 fps) can be associated with the acquisition of images associated with WL1, WL2, WL3, etc.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

In some implementations, source code can be human-readable code that can be written in program languages such as python, C++, etc. In some implementations, computer-executable codes can be machine-readable codes that can be generated by compiling one or more source codes. Computer-executable codes can be executed by operating systems (e.g., linux, windows, mac, etc.) of a computing device or distributed computing system. For example, computer-executable codes can include data needed to create runtime environment (e.g., binary machine code) that can be executed on the processors of the computing system or the distributed computing system.

Other embodiments are within the scope and spirit of the disclosed subject matter. For example, the prioritization method described in this application can be used in facilities that have complex machines with multiple operational parameters that need to be altered to change the performance of the machines. Usage of the word "optimize"/"optimizing" in this application can imply "improve"/"improving."

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a Read-Only Memory or a Random Access Memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web interface through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

What is claimed is:
1. A method, comprising:
receiving data characterizing a plurality of images of a surgical region comprising a first target tissue, the plurality of images comprising a plurality images associated with visible light images, a plurality of images associated with a first wavelength and a plurality of images associated with the second wavelength that is different from the first wavelength;

generating a first scene by at least overlaying a first set of images of the plurality of images, the first set of images being temporally contiguous, wherein the first set of images includes a first image associated with the first wavelength, a second image associated with visible light, and a third image associated with the second wavelength;

generating a second scene by at least overlaying a second set of images of the plurality of images, the second set of images being temporally contiguous, wherein the second set of images includes at least one image from the first set of images; and displaying the first scene and the second scene, wherein the first and the second scenes are displayed temporally contiguously.

2. The method of claim 1, wherein the at least one image from the first set of images that is included in the second set of images is the third image.

3. The method of claim 2, wherein generating the first scene includes:

generating a first tissue image of the first target tissue based on the first image and the third image; and overlaying the first tissue image on the second image associated with visible light.

4. The method of claim 3, wherein the first scene includes a first graphical object superimposed on or adjacent to the first tissue image in the first scene, the first graphical object configured to identify the first tissue image in the first scene.

5. The method of claim 3, wherein the second set of images includes the third image, a fourth image associated with visible light and a fifth image associated with the first wavelength.

6. The method of claim 5, wherein generating the second scene includes:

generating a second tissue image of the first target tissue based on the third image and the fifth image; and overlaying the second tissue image on the fourth image associated with visible light.

7. The method of claim 6, further comprising updating a location of the first graphical object to superimpose on or adjacent to the second tissue image of the first target tissue in the second scene, the updated first graphical object configured to identify the first target tissue in the second scene.

8. The method of claim 6, wherein the first, the second and the third images in the first set of images are captured temporally contiguously, and wherein the third, the fourth and the fifth images in the second set of images are captured temporally contiguously.

9. The method of claim 6, wherein the plurality of visible images are captured at between about 30 frames per second and about 60 frames per second.

10. The method of claim 9, wherein the plurality of images are captured by a sensor at 60 frames per second and the plurality of visible light images are captured by the sensor at 30 frames per second, and the plurality of images associated with the first and the second wavelength captured at 30 frames per second.

11. The method of claim 9, wherein the plurality of images are captured by a sensor at 120 frames per second and the plurality of visible light images are captured by the sensor at 30 frames per second, and the plurality of images associated with the first and the second wavelength captured at 90 frames per second.

12. The method of claim 1, wherein the plurality of images comprises a plurality of images associated with a third wavelength that is different from the first wavelength and the second wavelength, wherein the first set of images further includes a sixth image associated with the third wavelength, wherein the at least one image from the first set of images that is included in the second set of images includes the sixth image.

13. The method of claim 12, wherein generating the first scene includes:

generating a first tissue image of the first target tissue based on the first image and the third image;

generating a second tissue image of a second target tissue based on the third image and the sixth image, wherein the surgical region includes the second target tissue; and overlaying the first tissue image and the second tissue image on at least an image associated with visible light temporally contiguous with the third image and/or the sixth image.

14. The method of claim 13, wherein generating the second scene includes:

generating a third tissue image of the first target tissue based on the fifth image and a seventh image associated with the second wavelength, wherein the second set of images includes the seventh image;

generating a fourth tissue image of the second target tissue based on the sixth image and the seventh image; and overlaying the third tissue image and the fourth tissue image on at least an image associated with visible light temporally contiguous with the fifth image and/or seventh image.

15. The method of claim 14, wherein the plurality of visible images are captured at between about 30 frames per second and about 60 frames per second.

16. The method of claim 14, wherein the plurality of images are captured by a sensor at 60 frames per second and the plurality of visible light images are captured by the sensor at 30 frames per second, and the plurality of images associated with the first, the second and the third wavelength captured at 30 frames per second.

17. The method of claim 14, wherein the plurality of images are captured by a sensor at 120 frames per second and the plurality of visible light images are captured by the sensor at 30 frames per second, and the plurality of images associated with the first and the second wavelength captured at 90 frames per second.

18. The method of claim 14, wherein the second scene includes a first graphical object superimposed on or adjacent to the third tissue image of the first target tissue in the second scene, wherein the second scene includes a second graphical object superimposed on or adjacent to the fourth tissue image of the second target tissue.

19. The method of claim 14, further comprising displaying the first scene and the second scene, wherein the first tissue image and the second image are simultaneously displayed in the first scene.

20. The method of claim 13, wherein the at least one image from the first set of images that is included in the second set of images includes the third image and the sixth image.

21. The method of claim 20, wherein generating the second scene includes:

generating a sixth tissue image of the first target tissue based on the third image and the fifth image;

generating a sixth tissue image of the second target tissue based on the sixth image and the third image; and overlaying the fifth tissue image and the sixth tissue image on at least an image associated with visible light temporally contiguous with the fifth image and/or the sixth image.

22. The method of claim 21, wherein the plurality of visible images are captured at between about 30 frames per second and about 60 frames per second.

23. The method of claim 22, wherein the plurality of images are captured by a sensor at 60 frames per second and the plurality of visible light images are captured by the sensor at 30 frames per second, and the plurality of images associated with the first, the second and the third wavelength captured at 15 frames per second.

24. The method of claim 22, wherein the plurality of images are captured by a sensor at 120 frames per second and the plurality of visible light images are captured by the sensor at 30 frames per second, and the plurality of images associated with the first and the second wavelength captured at 90 frames per second.

25. The method of claim 21, wherein the second scene includes a first graphical object superimposed on or adjacent to the fifth tissue image of the first target tissue in the second scene, wherein the second scene includes a second graphical object superimposed on or adjacent to the sixth tissue image of the second target tissue.

26. A system comprising:
a single sensor configured to capture a plurality of images of a surgical region comprising a first target tissue, the plurality of images comprising a plurality of visible light images, first wavelength images and second wavelength images; and a processor configured to:
receive data characterizing the plurality of images of the surgical region comprising the first target tissue, the plurality of images comprising the plurality of visible light images, the plurality of first wavelength images and the plurality of second wavelength images;

generate a first scene by at least overlaying a first set of images of the plurality of images, the first set of images being temporally contiguous, wherein the first set of images includes a first image associated with a first wavelength, a second image associated with visible light, and a third image associated with a second wavelength;

generate a second scene by at least overlaying a second set of images of the plurality of images, the second set of images being temporally contiguous wherein the second set of images includes at least one image from the first set of images; and provide the first combined image and the second combined image, wherein the first and the second combined image are temporally contiguous.

27. The system of claim 26, wherein the sensor is operably associated with a surgical instrument.

28. The system of claim 27, wherein the surgical instrument includes one of an endoscope, a laparoscope, and a robotic vision system.

* * * * *